United States Patent [19]

Kramer et al.

[11] Patent Number: 4,727,061
[45] Date of Patent: Feb. 23, 1988

[54] PHARMACEUTICAL PREPARATIONS HAVING DIURETIC ACTIVITY

[75] Inventors: Herbert J. Kramer, Bonn; Klaus Lehmann, Rossdorf; Colin Liddiard, Weiterstadt, all of Fed. Rep. of Germany

[73] Assignee: Röhm GmbH, Darmstadt, Fed. Rep. of Germany

[21] Appl. No.: 805,871

[22] Filed: Dec. 6, 1985

[30] Foreign Application Priority Data

Dec. 17, 1984 [DE] Fed. Rep. of Germany ....... 3445933

[51] Int. Cl.[4] .............................................. A61K 37/02
[52] U.S. Cl. ..................................... 514/18; 514/19; 514/869
[58] Field of Search ........................... 514/18, 19, 869

[56] References Cited

U.S. PATENT DOCUMENTS 3,941,763  3/1976  Sarantakis ............................ 514/15
4,366,242  12/1986  Neumann et al. ...................... 435/7

OTHER PUBLICATIONS

Pettit, *Synthetic Peptides*, vol. 1, Van Nostrand Reinhold Co., N.Y. 1970, pp. 145, 156.
Brecher et al., *Chem. Abst.*, 72, 22 (1970), Abst. No. 284g.
Schmidbauer et al., *Angew. Chem.* 98 (1986), 1014–1015.
Ullmann's Encyclopedia of Industrial Chemistry, 5th Edn., vol. A4, pp. 519–531.

*Primary Examiner*—J. R. Brown
*Assistant Examiner*—F. T. Moezie
*Attorney, Agent, or Firm*—Curtis, Morris & Safford

[57] ABSTRACT

Pharmaceutical preparations having diuretic activity and comprising a peptide of the formula

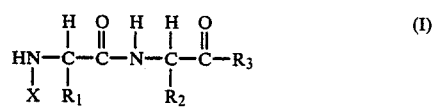

wherein (a) $R_1$ and $R_2$ are hydrogen and $R_3$ is —OH, or

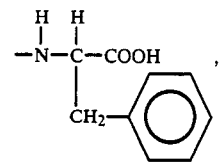

or Y, or
wherein (b) $R_1$ is hydrogen, $R_2$ is $CH_2OH$ or

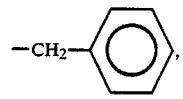

and $R_3$ is —OH or Y, or
wherein (c) $R_1$ is —$CH_2OH$ and $R_2$ is hydrogen or

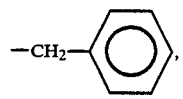

and $R_3$ is —OH or Y, or
wherein (d) $R_1$ is

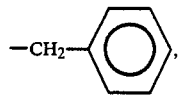

$R_2$ is hydrogen or —$CH_2OH$ and $R_3$ is —OH, —NHCH$_2$COOH, or Y, and
wherein
X is hydrogen, methyl, prolyl, or an N-protective group, and
Y is —NH$_2$, —OR$_4$, wherein R$_4$ is linear or branched alkyl or cyclolalkyl having from 1 to 8 carbon atoms, benzyl, phenyl, or

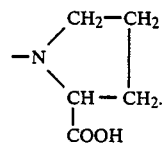

8 Claims, No Drawings

PHARMACEUTICAL PREPARATIONS HAVING DIURETIC ACTIVITY

The present invention relates to pharmaceutical preparations having diuretic activity, and especially natriuretic activity, the active ingredients of which are low molecular weight peptides, and to methods for inducing diuresis using such peptides.

These pharmaceutical preparations are suitable for use particularly in the case of syndromes where increased urine excretion is therapeutically desirable. It should be noted that what is being forced is, predominantly to exclusively, the excretion of the sodium salts, and especially of sodium chloride, but not of potassium salts. These pharmaceutical preparations lend themselves primarily to parenteral and, in particular, intravenous administration.

Substances which produce increased excretion of urea are generally known as diuretics.

The diuretics which are commonly used therapeutically can be classed on the type of their action, for example, and of the locus of action and mode of action, when known, and/or of their chemical structure.

Common classes are, for example, osmotic diuretics, carbonic anhydrase inhibitors, thiazide diuretics, loop diuretics, potassium-sparing diuretics, and diuretics which fall into none of these classes, for example the xanthines. (See Kirk-Othmer, 3rd ed., vol. 8, pp. 1-33, John Wiley & Sons, 1979.) These are all substances exogenous to the human body. Many are characterized by aromatic or heterocyclic structures.

These exogenous active substances usually have side effects which should not be neglected, particularly in long term therapy. For example, the use of diuretics may result in disturbances of the electrolyte balance, and especially hypokalemia. A subnormal potassium level in the serum can be prevented to some extent by potassium administration, but more effectively by the simultaneous administration of potassium retaining diuretics such as spironolactone, triamterene, or amiloride. It has been hypothesized for more than twenty-five years that there exists a natriuretic hormone which promotes sodium chloride excretion in the organism. While it has not been possible so far positively to identify such a natriuretic hormone, the results of activity determinations on model systems with serum and urine fractions from rats, dogs and healthy test persons treated with sodium chloride suggest that the putative natriuretic hormone is a relatively low molecular weight substance. [See H. J. Kramer et al., "Nachweis und Charakterisierung natriuretischer Faktoren in Plasma und Urin," abstract in Nieren- und Hochdruckkrankheiten 8, 236 (1979).] It is hypothesized that the mode of action of this natriuretic hormone (NH) is inhibition of $Na^+$-$K^+$- dependent ATPase (adenosinetriphosphatase), which influences the transepithelial sodium transport. [H. C. Conick et al. in Clin. Sci. Mol. Med. 53, 329-334 (1977).] The structure of this hypothetical natriuretic hormone must still be regarded as unknown.

Many oligopeptides found in the central nervous system have hormonal action. They affect the gastrointestinal region, for example, or have behavioral effects and exert a modifying influence on certain glandular functions. The small peptide hormones include thyroliberin (thyrotropin-releasing factor, TRF), which stimulates the secretion of the thyroid-stimulating hormone in rats and mice, and the enkephalins, which have been isolated only from the pituitary gland and which exert morphinomimetic activity.

The oligopeptides known collectively as brain oligopeptides are thought to have the function of extracellular messenger substances which may play an important role in the transmission of information and in neuroregulation. (See Kirk-Othmer, 3rd Ed., vol. 12, pp. 603-617, John Wiley & Sons, 1980.)

It is believed at present that the regulatory process takes place with the intervention of specific receptors. However, the interaction between messenger substances and receptor and the mechanism of the regulatory action have become clear only in isolated cases. Also, a specific modification in the sense of therapeutic intervention in the metabolism is involved only in relatively few cases.

While pharmaceutical principles are available in therapeutic practice for diuretic treatments tailored to specific cases, there is still uncertainty in individual cases as to how the organism will respond to the medication, what side effects the medication will have, and how the organism will react to long term administration of the medication.

Diuretic therapy is indicated in the case of:

1. Generalized edema with increased sodium reserves in the organism (chronic cardiac insufficiency, left ventricular insufficiency with pulmonary congestion and pulmonary edema, hepatic cirrhosis with ascites, renal dysfunction).

2. Local edemas.

3. Diuretic indications without edema (arterial hypertension, toxemia) and other indications such as diabetes insipidus, glaucoma, elimination of calcium potassium and magnesium, retention of potassium and magnesium, idiopathic edema. [See D. P. Morris in Arztblatt Baden-Worttemberg 3 (1974), where the therapeutic schemes which have evolved are also described.]

Thus there continues to be a need for diuretics which, while possessing adequate diuretic efficacy, produce as few adverse reactions, and especially side effects, as possible in the organism. The diuretically active principles should preferably cause no problems with respect to metabolisis. Moreover, they should be readily available and easy to handle, and it should be possible to prepare them in dosage forms of maximum stability.

Finally, there has been a need for a specific natriuretic active substance, in other words the diuresis should impair the potassium and magnesium metabolism as little as possible.

It has been found according to the present invention that certain peptides are particularly well suited for use as active substances in the therapy of disorders that can be positively influenced by diuresis. These are primarily those disorders mentioned earlier herein.

The peptides which in accordance with the invention are to be used as diuretically active substances are those of the formula

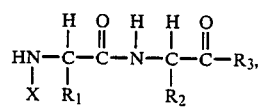

wherein (a) $R_1$ and $R_2$ are hydrogen and $R_3$ is —OH,

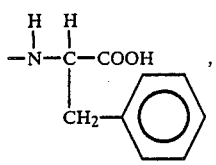

or Y; or wherein (b) R₁ is hydrogen, R₂ is CH₂OH or

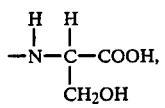

and R₃ is —OH or Y; or wherein (c) R₁ is —CH₂OH and R₂ is hydrogen or

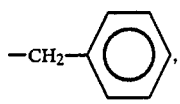

and R₃ is —OH or Y; or wherein (d) R₁ is

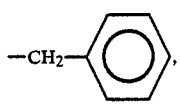

R₂ is hydrogen or —CH₂OH, and R₃ is —OH, —NHCH₂COOH or Y; and wherein X is hydrogen, methyl, prolyl, or an N-protective group; and wherein Y is —NH₂, —OR₄, where R₄ is linear or branched alkyl or cycloalkyl having 1 to 8 carbon atoms, benzyl, phenyl, or

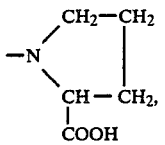

or precursors which under physiological conditions will form such peptides.

By an N-protective group is meant one of the usual protective groups (R. A. Boissonas in Advances in Organic Chemistry, vol. 3, pp. 159–183, Interscience, 1963), and in particular an N-acyl group such as a carboxyl ester group, for example carbobenzyloxy which may also be substituted with nitro, chloro, or phenylazo, carbotert-butyloxy, carbocyclopentyloxy, fatty acid carbonyl groups such as formyl or trifluoroacetyl, and aromatic acyl groups such as benzoyl, phthaloyl, and tosyl.

Illustrative of acylic R₄ groups are, in particular, methyl, ethyl, and tert-butyl, and, of cyclic R₄ groups, those having from 5 to 8 ring carbon atoms, especially cyclohexyl.

As is apparent from the foregoing formula, the peptides of the formula are made up of the amino acids glycine (Gly), phenylalanine (Phe), and serine (Ser). Not only the peptides derived from the naturally occurring L-amino acids, but also the racemates or the peptides formed from the corresponding D-amino acids are suitable for therapeutic use. As a rule, these are small peptides with three or two amino acids as building blocks. The peptides should either include at least one glycine or be made up of amino acids differing from one another.

Peptides in which glycine occupies the N-terminal position or the C-terminal position or both are preferred. On the whole, peptides containing two glycine residues, and particularly those with two linked glycine residues of which one is in the C-terminal position, are preferred. The following peptides are examples:

L-Phe-Gly-Gly
Gly-Gly
Gly-Gly-L-Phe
Gly-L-Phe
L-Phe-Gly
L-Ser-Gly
Gly-L-Ser
L-Phe-L-Ser.

As a rule, the peptides of the formula which are suitable for use in accordance with the invention are completely water soluble.

The peptides of the formula which are active in accordance with the invention are compounds of relatively simple structure, most of which are known. Their preparation is known or can be effected in known manner. (See Ullmanns Enzyklopadie der technischen Chemie, 4th ed., vol. 19, pp. 540–558, Verlag Chemie.) The corresponding D-amino acids suitable for use as building blocks are also known.

In the synthesis, the free hydroxyl group should be protected as tert-butyl ether when serine is present. The terminal carboxyl acid should be protected as an ester, and preferably as the methyl ester.

The terminal amino group should also be conventionally protected (cf. R. A. Boissonas in Advances in Organic Chemistry, vol. 3, pp. 159–190, R. Raphael et al., editors, Interscience Publishers, New York, 1963), for example by means of a carbobenzoxy group (Z). The building blocks are advantageously linked to one another through activated derivatives such as mixed anhydrides with chloroformate, for example. Alternatively, they may be linked by the use of carbodiimides as activating agents, for example with dicyclohexylcarbodiimide, optionally with the addition of racemization reducing additives such as 1-hydroxybenzotriazole, 3-hydroxy-4-oxo-3,4-dihydro-1,2,3-benzotriazine, or N-hydroxysuccinimide. The carbobenzoxy protective group (Z) is advantageously split off by catalytic hydrogenation. In this way a peptide is obtained which has a free NH group that can again be reacted with an N-protected amino acid.

The Z group is split off by catalytic hydrogenation, predominantly with palladium catalysts, at room temperature and normal pressure. The tert-butyl group serving as protective group for the hydroxyl group in the serine can be split off by acid solvolysis using trifluoroacetic acid. (See Houben-Weyl, Methoden der organischen Chemie, 4th ed., vol. 15, Georg Thieme Verlag, Stuttgart, 1974.) The ester group, for example an ethyl or methyl ester group, can be split off by hydrolysis, particularly with alkali, to yield the free peptide. Benzyl and nitrobenzyl esters can be split off by catalytic hydrogenation.

On the whole, the pharmaceutical preparations of the invention are intended more for parenteral administration than for oral administration. However, they can also be used orally, especially when they are appropriately coated to pass through the gastrointestinal tract without loss of activity prior to absorption. They lend themselves to intravenous, subcutaneous, or intramuscular administration. Absorption through the nasal mucous membranes might also be utilized in therapy.

As a rule, the pharmaceutical preparations of the invention are used in a daily dosage of 250 micrograms and up per kilogram of body weight. The daily intravenous dosage will generally range from 250 to 2500 micrograms/kg and, as a guide, should be about 500 micrograms/kg. The daily dosage for nasal and oral administration will be from 5 to 10 times greater and intramuscular daily dosages will have values between these extremes.

As mentioned earlier, the active substances of the invention are advantageously used in the form of solutions for intravenous administration, for example in the form of the solutions in an aqueous carrier appropriate to intravenous administration. As usual, the solutions must be sterile, capable of storage free of suspended matter, and pyrogen free in amounts of over 10 ml.

In the interest of compatibility, the liquid carrier is advantageously matched in the usual way to the blood serum. Care should therefore be taken to assure isotonicity and isohydricity with the blood serum. (See F. Gstirner, Einführung in die Verfahrenstechnik der Arzneiformen, 5th ed., pp. 255-307, Wissenschaftliche Verlagsgesellschaft, 1973.)

Administration of the pharmaceutical preparations of the invention in combination with parenterallly introduced nutrient solutions is particularly advantageous. In continuous infusions, solutions are introduced which contain mixtures of essential amino acids. The peptides of the foregoing formula to be used in accordance with the invention can advantageously be added to such continuous infusion solutions and administered as such.

A special advantage of the inventive pharmaceutical preparations containing the aforementioned peptides is that while they have natriuretic activity, that is cause increased sodium chloride excretion in comparison with the untreated state, they do not simultaneously result in substantially increased potassium excretion. In other words, the peptides exert specifically natriuretic activity.

Moreover, the combination of these natriuretically active peptides with so-called calcium antagonists is of interest.

By calcium antagonists are meant the calcium antagonistic inhibitors of electromechanical coupling. (See Ullmanns Enzyklopädie der technischen Chemie, 4th ed., vol. 10, P. 639.) Suitable participants are, for example, Verapamil, Methoxyverapamil, Gallopamil, Nifedipin, Prenylamin, Fendilin, and Diltiazem.

Some of the calcium antagonists to be used can be represented by the formula

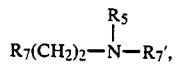

and/or the pharmacologically acceptable acid addition salts derived therefrom, wherein $R_5$ is hydrogen or methyl, $R_7$ and $R_7'$ are $(C_6H_5)_2CH-$ or

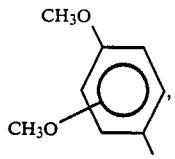

and $R_6$ is $-CH(CH_3)-(CH_2)_n-C_6H_5$ wherein n is 0 or 1, or

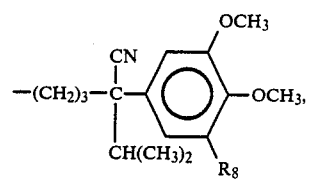

wherein $R_8$ is hydrogen or methoxy, with the condition that in a given molecule of this formula there may only be present at the same time either unsubstituted phenyl groups and a secondary nitrogen atom ($R_5$=hydrogen) or phenyl groups substituted with methoxy groups and a tertiary nitrogen atom ($R_5$=methyl).

The dosage of the calcium antagonists as a component of the inventive pharmaceutical preparations ranges from 0.5 to 20 mg/kg, and preferably from 5 to 15 mg/kg. They may be added to the preparations in conventional fashion. The diuretic activity, and more particularly the natriuretic and antikaliuretic activity, of the aforementioned peptides can be demonstrated in tests with rats, for example.

In the present case, the natriuretic activity is determined as described by H. G. Kramer, C. Rietzel, D. Klingmueller and R. Duesing in "Further Studies in Isolation and Purification of a Smaller Molecular Weight Natriuretic Hormone" in Lichardus, Schrier, Ponec, Hormonal Regulation of Sodium Excretion, Elsevier/North Holland, Amsterdam, 1980.

In the test protocol employed, female Sprague-Dawley rats weighing from 206 to 250 g were used as test animals. Before the test, the rats were exposed to a normal diet and had free access to food and water. On the day of the test, the rats were anesthetized with methohexital and catheters were inserted in the aorta and the jugular vein and from there through the abdomen in the bladder.

The animals were then placed into individual cages mounted on a scale. A 0.45% saline solution with 2.5% fructose was then administered to them intravenously at a rate ranging from 33 to 62 microliters per minute so that the body weight remained constant. Two hours after the animals had recovered, 15 minute urine collection periods were initiated and continued throughout the test. The diuretic material to be tested was dissolved (at pH 7.4) in the infusion solution, which contained tris HCl as a buffer. In the case of the fractions characterized by natriuresis, 15 minute urine samples were collected until the sodium excretion had again reached the base line, and the rate of infusion was adjusted so that the body weight remained constant. The arterial blood pressure was monitored throughout the test by means of a pressure measuring apparatus (Statham P-23-Db). The sodium and potassium concentrations in serum and urine were monitored by flame photometry. The sodium excretion corresponding to the median base line was 0.730±0.028 microequivalent/minute.

PROCEDURE 250 micrograms of the peptide substance to be tested were administered to each rat. The results presented in the Table below were obtained as follows:

(1) Sodium excretion in untreated rats (average values based on two to three individual assays) in micromoles of Na+ per minute.

(2) Sodium excretion in treated rats in micromoles per minute per milligram of administered substance of formula I.

(3) Time of maximum activity ($t_{max}$) in minutes.

(4) Increase in natriuresis as quotient F=(Na+ excretion after treatment)/(Na+ excretion before treatment).

TABLE

| Compound of formula (I) | (1) Na+ excretion | Q = K+/Na+ | (2) Na+ excretion | Q = K+/Na+ | (3) $t_{max}$ (minutes) | (4) F |
|---|---|---|---|---|---|---|
| Gly-Gly | 0.37 | 3.4 | 14.7 | 0.63 | 90–150 | 39.8 |
| L-Phe-Gly-Gly | 0.85 | 2.0 | 19.2 | 0.53 | 60–150 | 22.6 |
| Gly-Gly-L-Phe | 0.67 | 1.8 | 3.2 | 1.6 | 45–150 | 4.8 |
| L-Phe-L-Ser | 0.45 | 2.2 | 9.8 | 1.0 | 135–165 | 21.8 |
| Gly-L-Phe | 0.50 | — | 13.6 | — | 120–150 | 27.2 |
| L-Phe-Gly | 1.35 | — | 21.2 | — | 45–60 | 15.7 |
| L-Ser-Gly | 0.75 | — | 16.2 | — | 70–80 | 21.6 |
| Gly-L-Ser | 1.30 | — | 20.9 | — | 45–60 | 16.1 |

RESULTS

The animals treated in accordance with the invention exhibited a substantial increase in natriuresis after administration of the active substances of formula (I).

Similar results were obtained with L-Ser-Gly-Gly; L-Ser-L-Phe; Gly-Gly-L-Ser.

PHARMACEUTICAL PREPARATIONS FOR PERORAL USE

Tablets for peroral use containing the peptides which are active in accordance with the invention are prepared in the following way:

| peptide | 50–150 mg |
|---|---|
| cellulose, microcrystalline (AVICEL ®) | 98 mg |
| lactose, granulated | 250–150 mg |
| magnesium stearate | 2 mg |
| total | 400 mg |

The powdery peptide is mixed with the microcrystalline cellulose in a tumbling mixer, then granulated lactose is admixed and finally magnesium stearate is added. The mixture is treated in the tumbling mixer for another 20 minutes. Using a conventional tablet press, slightly curved circular tablets are pressed therefrom. The tablets thus obtained are subsequently coated with the following polymer solution to protect them against gastric fluids (based on 3 kg of tablet mass).

| a methylmethacrylate-methacrylic acid copolymer (1:1 by weight) | 85 g |
|---|---|
| polyethyleneglycol | 15 g |
| talcum | 50 g |
| water | 50 g |

| isopropanol | 400 g |
|---|---|
| acetone | 400 g |
| total | 1000 g |

The lacquer was applied in a conventional rotating drum using a spraying pistol operated by compressed air and was dried by warm air (ca. 30°–50° C.) within 2 hours.

We claim:

1. The method of inducing diureses in a patient in need of such treatment, which method comprises orally of parenterally administering to said patient a diuretically effective amount of peptide of the formula

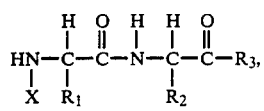

wherein (a) R₁ and R₂ are hydrogen and R₃ is —OH, or

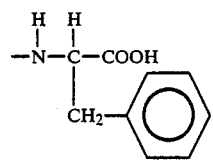

or

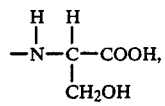

or Y, or wherein (b) R₁ is hydrogen, R₂ is —CH₂OH or

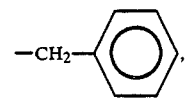

and and R₃ is —OH or Y, or
wherein (c) R₁ is —CH₂OH, R₂ is hydrogen or

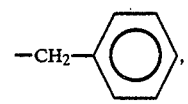

and R₃ is —OH or Y, or
wherein (d) R₁ is

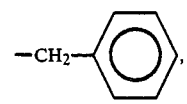

R₂ is hydrogen or —CH₂OH, and R₃ is —OH, —NHCH₂COOH, or Y,
wherein
X is hydrogen, methyl, prolyl, or an N-protective group, and Y is —NH₂, —OR₄, wherein R₄ is linear or branched alkyl or cycloalkyl having from 1 to 8 carbon atoms, benzyl, phenyl, or

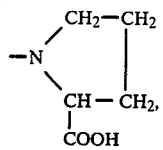

wherein those amino acids in said peptide having a chiral center are in the L-form.

2. A pharmaceutical preparation having diuretic activity, comprising a pharmaceutical carrier selected from the group consisting of orally-administrable and parenterally-administrable pharmaceutical carriers a calcium antaganist, and a diuretically effective amount of a peptide of the formula

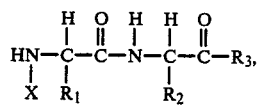

wherein (a) R₁ and R₂ are hydrogen and R₃ is —OH, or

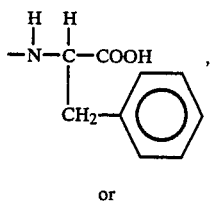

or

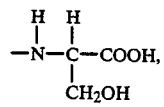

or Y, or
wherein (b) R₁ is hydrogen, R₂ is —CH₂OH or

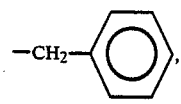

and R₃ is —OH or Y, or
wherein (c) R₁ is —CH₂OH, R₂ is hydrogen or

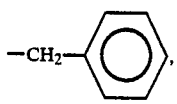

and R₃ is —OH or Y, or
wherein (d) R₁ is

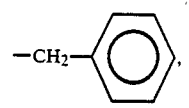

R₂ is hydrogen or —CH₂OH, and R₃ is —OH, —NHCH₂COOH, or Y,
wherein
X is hydrogen, methyl, prolyl, or an N-protective group, and
Y is —NH₂, —OR₄, wherein R₄ is linear or branched alkyl or cycloalkyl having from 1 to 8 carbon atoms, benzyl, phenyl, or

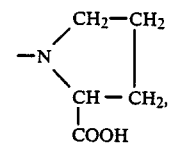

wherein those amino acids in said peptide having a chiral center are in the L-form.

3. A pharmaceutical preparation as in claim 2 wherein said pharmaceutical carrier is a parenterally-administrable carrier.

4. A pharmaceutical preparation as in claim 3 wherein said parenterally-administrable carrier is intravenously-administrable.

5. A pharmaceutical preparation as in claim 2 wherein said pharmaceutical carrier is an orally-administrable carrier.

6. A pharmaceutical preparation as in claim 2, wherein said peptide is selected from the group consisting of
Gly-Gly-L-Phe,
Gly-Gly,
Gly-Gly-L-Ser,
Gly-L-Ser, and
Gly-L-Phe.

7. A pharmaceutical preparation as in claim 2, wherein said peptide is selcted from the group consisting of
L-Phe-Gly-Gly,
L-Phe-Gly,
L-Phe-L-Ser-Gly, and
L-Phe-L-Ser.

8. A pharmaceutical preparation as in claim 2, wherein said peptide is selected from the group consisting of
L-Ser-Gly-Gly,
L-Ser-Gly,
L-Ser-L-Phe-Gly, and
L-Ser-L-Phe.

* * * * *